United States Patent
McGrew (10) Patent No.: US 6,632,637 B1
(45) Date of Patent: Oct. 14, 2003

(54) VECTORS AND METHODS FOR RECOMBINANT PROTEIN EXPRESSION

(75) Inventor: Jeffrey T. McGrew, Seattle, WA (US)

(73) Assignee: Immunex Corporation, Seattle, WA (US)

(*) Notice: Subject to any disclaimer, the term of this patent is extended or adjusted under 35 U.S.C. 154(b) by 16 days.

(21) Appl. No.: 09/687,050

(22) Filed: Oct. 12, 2000

Related U.S. Application Data (60) Provisional application No. 60/159,177, filed on Oct. 13, 1999.

(51) Int. Cl.[7] ............................ C12P 21/06; C07H 17/00
(52) U.S. Cl. .................... 435/69.1; 435/320.1; 435/325; 435/252.3; 536/23.1
(58) Field of Search ........................... 435/320.1, 69.1, 435/325, 70.1; 514/44

(56) References Cited

U.S. PATENT DOCUMENTS

| | | | |
|---|---|---|---|
| 4,937,190 A | * 6/1990 | Palmenberg et al. | ........ 435/68.1 |
| 5,741,682 A | * 4/1998 | Lo et al. | ...................... 435/375 |
| 6,027,915 A | 2/2000 | Morris et al. | |
| 6,165,715 A | 12/2000 | Collins et al. | |
| 6,312,951 B1 | 11/2001 | Morris et al. | |
| 2002/0123473 A1 | * 9/2002 | Nordstrom et al. | ............ 514/44 |

FOREIGN PATENT DOCUMENTS

| | | |
|---|---|---|
| WO | WO 96/33272 | 10/1996 |

OTHER PUBLICATIONS

Lucas et al., "High–level production of recombinant proteins in CHO celss using a dicistronic DHFR introm expression vector", Nucleic Acids Res. 24:1774–1779, 1996.*

Daveies and Kaufman, "Internal translation initiation in the design of improved expression vectors," Current Opion in Biotechnology 3:512–517, 1992.*

U.S. patent application Ser. No. 09/435,377, filed Nov. 1999, Morris et al.

Davies and Kaufman, "The sequence context of the initiation codon in the encephalomyocarditis virus leader modulates efficiency of internal translation initiation," J. Virol. 66:1924–1932, 1992.

Lucas et al., "High–level production of recombinant proteins in CHO cells using a dicistronic DHFR intron expression vector," Nucleic Acids Res. 24:1774–1779, 1996.

Kaufman, R.J., et al., "Improved vectors for stable expression of foreign genes in mammalian cells by use of the untranslated leader sequence from EMC virus," Nucleic Acids Res. 19:4485–4490, 1991.

Jang et al., "Initiation of protein synthesis by internal entry of ribosomes into the 5' nontranslated region of encephalomyocarditis virus RNA in vivo," J. Virol. 63:1651–1660, 1989.

(List continued on next page.)

*Primary Examiner*—Karen Cochrane Carlson
*Assistant Examiner*—Sheridan Snedden
(74) *Attorney, Agent, or Firm*—Patricia Anne Perkins; Kathleen Fowler (57) ABSTRACT

There is disclosed an expression vector utilizing an internal polyadenylation signal. The internal polyadenylation signal is inserted between a DNA encoding a protein of interest and a DNA encoding a selectable marker, and allows a single promoter to generate both monocistronic messages and dicistronic messages. Similar, multicistronic vectors can also be prepared. Also disclosed are methods of using the expression vector utilizing an internal polyadenylation signal, host cells transfected therewith, stable pools of cells transfected with an expression vector utilizing an internal polyadenylation signal, and clones of such transfected cells.

44 Claims, 1 Drawing Sheet

OTHER PUBLICATIONS

Carswell and Alwine, "Efficiency of utilization of the simian virus 40 late polyadenylation site: effects of upstream sequences," *Mol. Cell. Biol.* 9:4248–4258, 1989.

Davies and Kaufman, "Internal translation initiation in the design of improved expression vectors," *Current Opinion in Biotechnology* 3:512–517, 1992.

Fussenegger et al., "Autoregulated multicistronic expression vectors provide one–step cloning of regulated product gene expression in mammalian cells," *Biotechnol. Prog.* 13:733–740, 1997.

Gurtu, V. et al., "IRES Bicistronic expression vectors for efficient creation of stable mammalian cell lines," *Biochem Biophys Res Comm* 229:295–298, 1996.

Kaufman, R. et al., "Improved vectors for stable expression of foreign genes in mammalian cells by use of the untranslated leader sequence from EMC virus," *Nucleic Acids Res* 19(16):4485–4490, 1991.

* cited by examiner

Figure 1

VECTORS AND METHODS FOR RECOMBINANT PROTEIN EXPRESSION

This application claims the benefit of U.S. provisional application No. 60/159,177, filed Oct. 13, 1999.

TECHNICAL FIELD OF THE INVENTION

The present invention relates to expression of recombinant proteins in eukaryotic cells.

BACKGROUND OF THE INVENTION

The development of expression systems for production of recombinant proteins is important for providing a source of a given protein for research or therapeutic use. Expression systems have been developed for both prokaryotic cells, such as E. coli, and for eukaryotic cells, such as yeast (i.e., Saccharomyces, Pichia and Kluyveromyces spp) and mammalian cells. Expression in mammalian cells is often preferred for manufacturing of therapeutic proteins, since post-translational modifications in such expression systems are more likely to resemble those occurring on endogenous proteins in a mammal, than the type of post-translational modifications that occur in microbial expression systems.

Several vectors are available for expression in mammalian hosts, each containing various combinations of cis- and in some cases trans-regulatory elements to achieve high levels of recombinant protein in a minimal time frame. However, despite the availability of numerous such vectors, the level of expression of a recombinant protein achieved in mammalian systems is often lower than that obtained with a microbial expression system. Additionally, because only a small percentage of cloned, transfected mammalian cells express high levels of the protein of interest, it can often take a considerably longer time to develop useful stably transfected mammalian cell lines than it takes for microbial systems.

The use of a dicistronic expression vector wherein a first open reading frame encodes a polypeptide of interest and a second open reading frame encodes a selectable marker, is one method that has been used to obtain recombinant proteins. A preferred marker for use in such systems is dihydrofolate reductase (DHFR), which has the advantage of being an amplifiable gene, allowing selection for cells having high copy numbers of the inserted DNA by culturing them in increasing levels of methotrexate (MTX). However, translation of the selectable marker gene is up to 100-fold less efficient than translation of the gene of interest, which reduces the efficiency of the selection process. Moreover, dicistronic expression vectors tend to undergo deletion or rearrangement under amplification conditions, in an uncontrolled manner, increasing the chances that amplified cells will no longer express the protein of interest. Internal ribosome entry sites (IRES) are a type of regulatory element found in several viruses and cellular RNAs (reviewed in McBratney et. al. Current Opinion in Cell Biology 5:961, 1993). IRES increase the efficiency of translation of the selectable marker gene, and are thus useful in enhancing both the selection and amplification process (Kaufman R. J., et al., Nucleic Acids Res. 19:4485, 1991). Nonetheless, the available evidence indicates that dicistronic mRNAs accumulate to lower levels than monocistronic mRNAs, possibly because of reduced mRNA stability of the longer message.

Because the amount of recombinant protein produced by a transfected cell is generally proportional to the amount of mRNA available for translation of the protein, the use of dicistronic expression vectors may result in low levels of production of the desired recombinant protein. Accordingly, there is a need in the art to develop improved methods that retain the utility of a selectable, amplifiable marker such as DHFR, while increasing the proportion of mRNAs encoding the desired recombinant protein. Moreover, there is a need to develop methods that facilitate selection of those transfectants that integrate into more transcriptionally active sites, and that allow production of useful levels of recombinant protein from mammalian cells in a relatively short period of time.

SUMMARY OF THE INVENTION

In one embodiment of the invention, an expression vector comprises a DNA encoding a first protein, operably linked to a DNA encoding a second protein, wherein a DNA encoding a polyadenylation (polyA) site is inserted between the DNA encoding the first protein of interest and the DNA encoding the second protein, such that the DNA encoding the internal polyadenylation site is operably linked to the DNA encoding the first. A preferred second protein is selectable marker, preferably dihydrofolate reductase (DHFR); other amplifiable markers are also suitable for use in the inventive expression vectors.

Preferably, the polyadenylation signal utilized to provide the internal polyadenylation site is an SV40 polyadenylation signal, more preferably, the late SV40 polyadenylation signal, and most preferably, a mutant version of the late SV40 polyadenylation signal. The preferred polyadenylation signals are presented in the Sequence Listing and described further below. In another embodiment of the invention, the polyadenylation signal is inducible.

The expression vector may further comprise an IRES sequence between the DNA encoding the first protein, and the DNA encoding the second protein, operably linked to both and downstream of the internal polyadenylation site. Alternatively, the expression vector may comprise mRNA splice donor and acceptor sites substantially as described by Lucas et al. infra.

Another aspect of the invention comprises an expression vector into which a DNA encoding a protein. Such an expression vector comprises a site into which a DNA encoding a recombinant, heterologous protein can be inserted (referred to as a cloning site), such that it is operably linked to an internal polyadenylation site and a DNA encoding a second protein (such as a selectable marker). Optionally, other regulatory elements may also be included, for example, an IRES sequence downstream of the internal polyadenylation site, or mRNA splice donor and acceptor sites substantially as described by Lucas et al. infra, operably linked to the internal polyadenylation site and the DNA encoding the second protein. An expression-augmenting sequence element (EASE) may also be included upstream of the cloning site, operably linked thereto.

Host cells can be transfected with the inventive expression vectors, yielding stable pools of transfected cells. Accordingly, another embodiment of the invention provides a transfected host cell; yet another embodiment provides a stable pools of cells transfected with the inventive expression vector. Also provided are cell lines cloned from pools of transfected cells. Preferred host cells are mammalian cells. In a most preferred embodiment, the host cells are CHO cells.

The invention also provides a method for obtaining a recombinant protein, comprising transfecting a host cell with an inventive expression vector, culturing the transfected host cell under conditions promoting expression of the protein, and recovering the protein. In a preferred application of this invention, transfected host cell lines are selected with two selection steps, the first to select for cells expressing the dominant amplifiable marker, and the second step for high expression levels and/or amplification of the marker gene as well as the gene of interest. In a most preferred embodiment, the selection or amplification agent is methotrexate, an inhibitor of DHFR that has been shown to cause amplification of endogenous DHFR genes and transfected DHFR sequences.

DETAILED DESCRIPTION OF THE INVENTION

Expression vectors that retain the utility of a selectable, amplifiable marker such as DHFR, while increasing the proportion of mRNAs encoding a desired recombinant protein, are provided herein. The inventive expression vectors comprise a polyadenylation signal inserted between a first coding sequence and a second or subsequent coding sequence (referred to as an internal polyadenylation site). In the inventive vectors, transcripts originating at the promoter can be polyadenylated following the first coding sequence (monocistronic message) or after the second or subsequent coding sequence (multicistronic message). In one embodiment of the invention, the first coding sequence encodes a protein of interest, and the second (or subsequent) coding sequence encodes a selectable marker. In another embodiment, a second polyadenylation site follows the second or subsequent coding sequence, and is operably linked thereto. In this embodiment, the internal polyadenylation site thus becomes the first polyadenylation site.

Because many transcripts encode only the gene of interest and not the selectable marker, the inventive vectors produce less selectable marker protein, and only those transfectants that integrate into more transcriptionally active sites survive the selection process. Accordingly, use of the inventive expression vectors facilitates isolation of transfected pools and clones that express high levels of recombinant protein using lower levels of a selection agent than is possible in the absence of the internal polyadenylation signal.

An additional benefit of utilizing the inventive expression vectors is that monocistronic messages may be more stable or more efficiently processed than dicistronic messages, potentially leading to increased accumulation of the message encoding the protein of interest, and hence to higher levels of protein production. Use of the inventive internal polyadenylation site will thus facilitate production of useful levels of recombinant protein by transfected cells in a relatively short period of time.

The inventive vectors and methods will also be useful in developing multicistronic vectors. Multicistronic expression vectors allow the coordinated expression of two or more genes (see, for example, Fussenegger et al., *Biotechnol Prog* 13:733; 1997). Inserting a polyadenylation site after a first cistron would result in high level expression of the first cistron and lower level expression of any following cistrons. Potential applications of this technology would be to facilitate expression of large amounts of a therapeutic protein (or other, desired recombinant proteins) and lower amounts of other proteins such as selectable markers, transcription factors, enzymes involved in protein folding, and other proteins that regulate cell metabolism and expression.

In another embodiment, the polyadenylation site is inserted after the second or third (or subsequent) cistron. This would allow high expression of the first two (or three or more) cistrons, followed by lower expression of the cistron following the internal polyadenylation site. This embodiment will find use, for example, in recombinant antibody synthesis where the heavy and light chains are synthesized independently at high levels. A tricistronic vector is constructed with the heavy and light chains encoded by the first two cistrons. The polyadenlyation site is inserted following the second cistron allowing high level expression of the first two cistrons. The selectable marker is expressed from the third cistron (i.e., after the polyadenylation site) and would be expressed at lower levels.

Expression of Recombinant Proteins

As used herein, the term 'expression vector' is understood to describe a vector that comprises various regulatory elements, described in detail below, that are necessary for the expression of recombinant, heterologous proteins in cells. The expression vector can include signals appropriate for maintenance in prokaryotic or eukaryotic cells, and/or the expression vector can be integrated into a chromosome.

Recombinant expression vectors may include a coding sequence encoding a protein of interest (or fragment thereof), ribozymes, ribosomal mRNAs, antisense RNAs and the like. Preferably, the coding sequence encodes a protein or peptide. The coding sequence may be synthetic, a cDNA-derived nucleic acid fragment or a nucleic acid fragment isolated by polymerase chain reaction (PCR). The coding sequence is operably linked to suitable transcriptional or translational regulatory elements derived from mammalian, viral or insect genes. Such regulatory elements include a transcriptional promoter, a sequence encoding suitable mRNA ribosomal binding sites, and sequences which control the termination of transcription and translation (i.e., a polyadenylation signal), as described in detail below.

Expression vectors may also comprise non-transcribed elements such as a suitable promoter and/or enhancer linked to the gene to be expressed, other 5' or 3' flanking non-transcribed sequences, 5' or 3' non-translated sequences such as ribosome binding sites, a polyadenylation site, splice donor and acceptor sites, and transcriptional termination sequences. An origin of replication that confers the ability to replicate in a host, and a selectable gene to facilitate recognition of transfectants, may also be incorporated.

DNA regions are operably linked when they are functionally related to each other. For example, DNA for a signal peptide (secretory leader) is operably linked to DNA for a polypeptide if it is expressed as a precursor which participates in the secretion of the polypeptide; thus, in the case of DNA encoding secretory leaders, operably linked means contiguous and in reading frame. A promoter is operably linked to a coding sequence if it controls the transcription of the sequence; and a ribosome binding site is operably linked to a coding sequence if it is positioned so as to permit translation.

Dicistronic expression vectors used for the expression of multiple transcripts have been described previously (Kim S. K. and Wold B. J., *Cell* 42:129, 1985; Kaufman et al. 1991, supra). Dicistronic expression vectors comprise two cistrons, or open reading frames, capable of encoding two proteins, for example, a recombinant of interest and a selectable marker. An example of such dicistronic expression vector is pCAVDHFR, a derivative of pCD302 (Mosley et al., *Cell* 1989) containing the coding sequence for mouse DHFR (Subramani et al., *Mol. Cell. Biol.* 1:854, 1981). Another example of such distronic expression vector is pCDE vector, a derivative of pCAVDHFR containing the murine encephalomyocarditis virus internal ribosomal entry site (nucleotides 260 through 824; Jang and Wimmer, *Genes and Dev.* 4:1560, 1990) cloned between the adenovirus tripartite leader and the DHFR cDNA coding sequence. Other types of expression vectors will also be useful in combination with the invention, for example, those described in U.S. Pat. Nos. 4,634,665 (Axel et al.) and 4,656,134 (Ringold et al.).

The transcriptional and translational control sequences in expression vectors to be used in transfecting cells may be provided by viral sources. For example, commonly used promoters and enhancers are derived from Polyoma, Adenovirus 2, Simian Virus 40 (SV40), and human cytomegalovirus. Viral genomic promoters, control and/or signal sequences may be utilized to drive expression, provided such control sequences are compatible with the host cell chosen. Examples of such vectors can be constructed as disclosed by Okayama and Berg (*Mol. Cell. Biol.* 3:280, 1983). Non-viral cellular promoters can also be used (i.e., the beta-globin and the EF-1alpha promoters), depending on the cell type in which the recombinant protein is to be expressed.

DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., *Nature* 273:113, 1978). Smaller or larger SV40 fragments may also be used, provided the approximately 250 bp sequence extending from the Hind III site toward the BglI site located in the viral origin of replication is included.

In dicistronic expression vectors, a polyadenylation site inserted downstream of, and operably linked to, the second cistron (usually, a DNA encoding a selectable marker), is often used to regulate transcription and translation. Many such polyadenylation signal are known (see for example, Table 1 below). The present invention utilizes an internal polyadenylation signal, eg., one that is inserted between the two cistrons of a dicistronic expression vector, in addition to a polyadenylation signal or other suitable regulatory element downstream of the second cistron.

Both the early and late polyadenylation signals of SV40 are useful in the instant invention. These sequences are encoded within the 237-base pair fragment between the BamnHI site at nucleotide 2533 and the BclI site at nucleotide 2770 of the SV40 genome (Carswell and Alwine, *Mol. Cell. Biol.* 9:4248; 1989). Carswell and Alwine concluded that, of the two SV40 polyadenylation signals, the late signal was more efficient, most likely because it comprises both downstream and upstream sequence elements that facilitate efficient cleavage and polyadenylation.

Many polyadenylation signals are known in the art, and will also be useful in the instant invention. Examples include those shown in Table 1 below.

TABLE 1

Polyadenylation Signals

| | |
|---|---|
| SV40 late polyA and deletion mutants thereof | Schek, N, Cooke, C., and J. C. Alwine (1992): Definition of the upstream efficiency element of the simian virus 40 late polyadenylation signal by using in vitro analysis. Mol. Cell Biol. 12:5386–5393 |
| HIV-1 polyA | Klasens, B. I. F., Das, A. T., and B. Berkhout (1998): Inhibition of polyadenylation by stable RNA secondary structure. Nucleic Acids Res. 26:1870–1876 |
| β-globin polyA | Gil, A., and N. J. Proudfoot. (1987): Position-dependent sequence elements downstream of AAUAAA are required for efficient rabbit β-globin mRNA formation. Cell 49:399–406 |
| HSV TK polyA | Cole, C. N. and T. P. Stacy (1985): Identification of sequence in the herpes simplex virus thymidine kinase gene required for efficient processing and polyadenylation. Mol. Cell. Biol. 5:2104–2113 |
| Polyomavirus polyA | Batt, D. B and G. G. Carmichael (1995): Characterization of the polyomavirus late polyadenylation signal. Mol. Cell. Biol. 15:4783–4790 |
| Bovine growth hormone | Gimmi, E. R., Reff, M. E., and I. C. Deckman. (1989): Alterations in pre-mRNA topology of the bovine growth hormone polyadenylation region decrease polyA site efficiency. Nucleic Acids Res. 17:6983–6998 |

Additional polyadenylation sites can be identified or constructed using methods that are known in the art. A minimal polyadenylation site is composed of AAUAAA and a second recognition sequence, generally a G/U rich sequence, found about 30 nucleotides downstream. In the Sequence Listing, the sequences are presented as DNA, rather than RNA, to facilitate preparation of suitable DNAs for incorporation into expression vectors. When presented as DNA, the polyadenylation site is composed of AATAAA, with, for example, a G/T rich region downstream (see for example, nucleotides 123 through 128 and 151 through 187, respectively, of SEQ ID NO:1).

Both sequences must be present to form an efficient polyadenylation site. The purpose of these sites is to recruit specific RNA binding proteins to the RNA. The AAUAAA binds cleavage polyadenylation specificity factor (CPSF; Murthy K. G., and Manley J. L. (1995), *Genes Dev* 9:2672–2683), and second site, frequently a G/U sequence, binds to Cleavage stimulatory factor (CstF; Takagaki Y. and Manley J. L. (1997) *Mol Cell Biol* 17:3907–3914). CstF is composed of several proteins, but the protein responsible for RNA binding is CstF-64, a member of the ribonucleoprotein domain family of proteins (Takagaki et al. (1992) *Proc Natl Acad Sci USA* 89:1403–1407).

The concentration of CstF-64 protein has been shown to be important in regulating usage of different polyadenylation sites in B-cells (Takagaki Y, Manley J L (1998) *Mol Cell* 2:761–771) Accordingly, an inducible polyadenylation site can be constructed based on this naturally occurring regulation of polyadenylation usage in B-cell, by controlling the interaction of CstF-64 with an mRNA of choice to induce polyadenylation. For example, the CstF-64 may be fused to the RNA binding domain of the MS2 phage coat protein, which binds a specific RNA sequence (ACAUGAGGAUUACCCAUGU; SEQ ID NO:4) distinct from the G/U rich element (Lowary and Uhlenbeck (1987) *Nucleic Acids Res.* 15:10483+10493). The target mRNA would contain an AAUAAA sequence and an MS2 coat protein RNA recognition sequence. By regulating the level of the MS2-CstF-64 fusion protein transcriptionally using standard inducible expression systems (for example, an Ecdysone-inducible mammalian expression system described by No et al. (1996) *Proc Natl Acad Sci USA* 93:3346–3351), the usage of the inducible polyA site could be controlled.

Polyadenylation may also be regulated by developing temperature-sensitive MS2 RNA binding domain mutants. MS2 RNA binding domain mutants may be generated using random mutagenesis, and screened for temperature sensitivity. When used as a fusion partner with CstF-64 as described above, the temperature-sensitive MS2 coat protein would be inactive and fail to bind RNA at 37° C.; thus the internal polyA site would not function at this temperature. However, at reduced temperature, for example 32° C., the MS2 coat protein would be active, would recognize the RNA sequence target, and the message would be polyadenylated. Temperature regulation would be particularly useful for recombinant protein expression, since reducing the temperature of expression cultures is typically used to increase protein expression.

An additional technique that can be used in conjunction with the inventive vectors is described by Lucas et al. (*Nucleic Acids Res.* 24:1774; 1996). In an effort to increase production of a desired protein, Lucas et al. utilized mRNA splice donor and acceptor sites to develop stable clones that produced both a selectable marker and recombinant proteins. According to these investigators, the vectors they prepared resulted in the transcription of a high proportion of mRNA encoding the desired protein, and a fixed, relatively low level of the selection marker that allowed selection of stable transfectants.

Host Cells

Transfected host cells are cells which have been transfected (sometimes referred to as transformed) with heterologous DNA. Many techniques for transfecting cells are known; in one approach, cells are transfected with expression vectors constructed using recombinant DNA techniques and which contain sequences encoding recombinant proteins. Expressed proteins will preferably be secreted into the culture supernatant, but may be associated with the cell membrane, depending on the particular polypeptide that is expressed. Mammalian host cells are preferred for the instant invention. Various mammalian cell culture systems can be employed to express recombinant protein. Examples of suitable mammalian host cell lines include the COS-7 lines of monkey kidney cells, described by Gluzman (*Cell* 23:175, 1981), CV-1/EBNA (ATCC CRL 10478), L cells, C127, 3T3, Chinese hamster ovary (CHO), HeLa and BHK cell lines.

A commonly used cell line is DHFR– CHO cells which are auxotrophic for glycine, thymidine and hypoxanthine, and can be transformed to the DHFR+ phenotype using DHFR cDNA as an amplifiable dominant marker. One such DHFR– CHO cell line, DXB11, was described by Urlaub and Chasin (*Proc. Natl. Acad. Sci. USA* 77:4216, 1980). Another example of a DBFR– CHO cell line is DG44 (see, for example, Kaufman, R. J., *Meth. Enzymology* 185:537 (1988)). Other cell lines developed for specific selection or amplification schemes will also be useful with the invention.

Numerous other eukaryotic cells will also be useful in the present invention, including cells from other vertebrates, and insect cells. Those of skill in the art will be able to select appropriate vectors, regulatory elements, transfection and culture schemes according to the needs of their preferred culture system.

Preparation of Transfected Mammalian Cells

Several transfection protocols are known in the art, and are reviewed in Kaufman, R. J., supra. The transfection protocol chosen will depend on the host cell type and the nature of the protein of interest, and can be chosen based upon routine experimentation. The basic requirements of any such protocol are first to introduce DNA encoding the protein of interest into a suitable host cell, and then to identify and isolate host cells which have incorporated the heterologous DNA in a stable, expressible manner.

One commonly used method of introducing heterologous DNA is calcium phosphate precipitation, for example, as described by Wigler et al. (*Proc. Natl. Acad. Sci. USA* 77:3567, 1980). DNA introduced into a host cell by this method frequently undergoes rearrangement, making this procedure useful for cotransfection of independent genes.

Polyethylene-induced fusion of bacterial protoplasts with mammalian cells (Schaffner et al., *Proc. Natl. Acad. Sci. USA* 77:2163, 1980) is another useful method of introducing heterologous DNA. Protoplast fusion protocols frequently yield multiple copies of the plasmid DNA integrated into the mammalian host cell genome. This technique requires the selection and amplification marker to be on the same plasmid as the gene of interest.

Electroporation can also be used to introduce DNA directly into the cytoplasm of a host cell, as described by Potter et al. (*Proc. Natl. Acad. Sci. USA* 81:7161, 1988) or Shigekawa and Dower (*BioTechniques* 6:742, 1988). Unlike protoplast fusion, electroporation does not require the selection marker and the gene of interest to be on the same plasmid.

More recently, several reagents useful for introducing heterologous DNA into a mammalian cell have been described. These include Lipofectin® Reagent and Lipofectamine™ Reagent (Gibco BRL, Gaithersburg, Md.). Both of these reagents are commercially available reagents used to form lipid-nucleic acid complexes (or liposomes) which, when applied to cultured cells, facilitate uptake of the nucleic acid into the cells.

Transfection of cells with heterologous DNA and selection for cells that have taken up the heterologous DNA and express the selectable marker results in a pool of transfected cells. Individual cells in these pools will vary in the amount of DNA incorporated and in the chromosomal location of the transfected DNA. After repeated passage, pools frequently lose the ability to express the heterologous protein. To generate stable cell lines, individual cells can be isolated from the pools and cultured (a process referred to as cloning), a laborious time consuming process. However, in some instances, the pools them selves may be stable (i.e., production of the heterologous recombinant protein remains stable). The ability to select and culture such stable pools of cells would be desirable as it would allow rapid production of relatively large amounts of recombinant protein from mammalian cells.

A method of amplifying the gene of interest is also desirable for expression of the recombinant protein, and typically involves the use of a selection marker (reviewed in Kaufman, R. J., supra). Resistance to cytotoxic drugs is the characteristic most frequently used as a selection marker, and can be the result of either a dominant trait (i.e., can be used independent of host cell type) or a recessive trait (i.e., useful in particular host cell types that are deficient in whatever activity is being selected for). Several amplifiable markers are suitable for use in the inventive expression vectors (for example, as described in Maniatis, *Molecular Biology: A Laboratory Manual*, Cold Spring Harbor Laboratory, NY, 1989; pgs 16.9–16.14).

Useful selectable markers for gene amplification in drug-resistant mammalian cells are shown in Table 1 of Kaufman, R. J., supra, and include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin. Specific examples of genes that encode selectable markers are those that encode antimetabolite resistance such as the DHFR protein, which confers resistance to methotrexate (Wigler et al., 1980, *Proc. Natl. Acad. Sci. USA* 77:3567; O'Hare et al., 1981, *Proc. Natl. Acad. Sci. USA* 78:1527); the GPT protein, which confers resistance to mycophenolic acid (Mulligan & Berg, 1981, *Proc. Natl. Acad. Sci. USA* 78:2072), the neomycin resistance marker, which confers resistance to the aminoglycoside G-418 (Colberre-Garapin et al., 1981, *J. Mol. Biol.* 150:1); the Hygro protein, which confers resistance to hygromycin (Santerre et al., 1984, *Gene* 30:147); and the Zeocin™ resistance marker (available commercially from Invitrogen). In addition, the herpes simplex virus thymidine kinase (Wigler et al., 1977, *Cell* 11:223), hypoxanthine-guanine phosphoribosyltransferase (Szybalska & Szybalski, 1962, *Proc. Natl. Acad. Sci. USA* 48:2026), and adenine phosphoribosyltransferase (Lowy et al., 1980, Cell 22:817) genes can be employed in tk-, hgprt- and aprt-cells, respectively.

Other dominant selectable markers include microbially derived antibiotic resistance genes, for example neomycin, kanamycin or hygromycin resistance. However, these selection markers have not been shown to be amplifiable (Kaufman, R. J., supra,). Several suitable selection systems exist for mammalian hosts (Maniatis supra, pgs 16.9–16.15). Co-transfection protocols employing two dominant selectable markers have also been described (Okayama and Berg, *Mol Cell Biol* 5:1136, 1985).

A particularly useful selection and amplification scheme utilizes DHFR-MTX resistance. MTX is an inhibitor of DHFR that has been shown to cause amplification of endogenous DHFR genes (Alt F. W., et al., *J Biol Chem* 253:1357, 1978) and transfected DHFR sequences (Wigler M., et al., *Proc. Natl. Acad. Sci. USA* 77:3567, 1980). Cells are transfected with DNA comprising the gene of interest and DNA encoding DHFR in a dicistronic expression unit (Kaufman et al., 1991 supra and Kaufman R. J., et al., *EMBO J* 6:187, 1987). Transfected cells are grown in media containing successively greater amounts of MTX, resulting in greater expression of the DHFR gene, as well as the gene of interest.

Useful regulatory elements, described previously, can also be included in the plasmids or expression vectors used to transfect mammalian cells. The transfection protocol chosen, and the elements selected for use therein, will depend on the type of host cell used. Those of skill in the art are aware of numerous different protocols and host cells, and can select an appropriate system for expression of a desired protein, based on the requirements of their selected cell culture system(s).

Uses of the Invention

The inventive vectors and methods will find use for the expression of a wide variety of recombinant polypeptides. Examples of such polypeptides include cytokines and growth factors, such as Interleukins 1 through 18, the interferons, RANTES, lymphotoxin-β, Fas ligand, flt-3 ligand, ligand for receptor activator of NF-kappa B (RANKL), TNF-related apoptosis-inducing ligand (TRAIL), CD40 ligand, Ox40 ligand, 4-1BB ligand (and other members of the TNF family), thymic stroma-derived lymphopoietin, granulocyte colony stimulating factor, granulocyte-macrophage colony stimulating factor, mast cell growth factor, stem cell growth factor, epidermal growth factor, growth hormone, tumor necrosis factor, leukemia inhibitory factor, oncostatin-M, and hematopoietic factors such as erythropoietin and thrombopoietin.

Also included are neurotrophic factors such as brain-derived neurotrophic factor, ciliary neurotrophic factor, glial cell-line derived neurotrophic factor and various ligands for cell surface molecules Elk and Hek (such as the ligands for eph-related kinases, or LERKS). Descriptions of proteins that can be expressed according to the inventive methods may be found in, for example, *Human Cytokines: Handbook for Basic and Clinical Research, Vol. II* (Aggarwal and Gutterman, eds. Blackwell Sciences, Cambridge Mass., 1998); *Growth Factors:A Practical Approach* (McKay and Leigh, eds., Oxford University Press Inc., New York, 1993) and *The Cytokine Handbook* (A W Thompson, ed.; Academic Press, San Diego Calif.; 1991).

Receptors for any of the aforementioned proteins may also be expressed using the inventive vectors and methods, including both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR).

Other proteins that can be expressed using the inventive vectors and methods include cluster of differentiation antigens (referred to as CD proteins), for example, those disclosed in *Leukocyte Typing VI* (*Proceedings of the VIth International Workshop and Conference*; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 4-1BB ligand and OX40 ligand); accordingly, members of the TNF and TNFR families can also be expressed using the present invention.

Proteins that are enzymatically active can also be expressed according to the instant invention. Examples include metalloproteinase-disintegrin family members, various kinases (including streptokinase and tissue plasminogen activator as well as Death Associated Kinase Containing Ankyrin Repeats, and IKR 1 and 2), TNF-alpha Converting Enzyme, and numerous other enzymes. Ligands for enzymatically active proteins can also be expressed by applying the instant invention.

The inventive vectors and methods are also useful for expression of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., *Biotechnology* 7:934–938, 1989; Reichmann et al., *Nature* 332:323–327, 1988; Roberts et al., *Nature* 328:731–734, 1987; Verhoeyen et al., *Science*

239:1534-1536, 1988; Chaudhary et al., *Nature* 339:394–397, 1989).

Various fusion proteins can also be expressed using the inventive methods and vectors. Examples of such fusion proteins include proteins expressed as fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are readily applicable to other proteins.

As additional examples, DNAs based on one or more expressed sequence tag (EST) from a library of ESTs can be prepared, inserted into the inventive vector and expressed to obtain recombinant polypeptide. Moreover, DNAs isolated by use of ESTs (i.e., by PCR or the application of other cloning techniques) can also be expressed by applying the instant invention. Information on the aforementioned polypeptides, as well as many others, can be obtained from a variety of public sources, including electronic databases such as GenBank. A particularly useful site is the website of the National Center for Biotechnology Information/National Library of Medicine/National Institutes of Health. Those of ordinary skill in the art are able to obtain information needed to express a desired polypeptide and apply the techniques described herein by routine experimentation.

However, for purposes of this application, the definition of a protein of interest excludes genes encoding proteins that are typically used as selectable markers in cell culture such as auxotrophic, antimetabolite and/or antibiotic markers. Nevertheless, the invention does include the use of a selectable marker as an aid in selecting cells and/or amplifying clones that are genetically engineered to express a gene of interest. Preferably, the selectable marker gene is positioned adjacent to the gene of interest such that selection and/or amplification of the marker gene will select and/or amplify the adjacent gene.

The relevant disclosures of all references cited herein are specifically incorporated by reference. The following examples are intended to illustrate particular embodiments, and not limit the scope, of the invention. Those of ordinary skill in the art will readily recognize that additional embodiments are encompassed by the invention.

EXAMPLES

Example 1

This example describes the preparation of several expression vectors for the expression of a soluble form of a receptor for human Interleukin-4, referred to as sIL-4R. Human IL-4R cDNA and protein are disclosed in U.S. Pat. Nos. 5,840,869, issued Nov. 24, 1998; 5,599,905, issued Feb. 4, 1997 and 5,856,296, issued Jan. 5, 1999. SEQ ID NOs:5 and 6 present the nucleotide and amino acid sequence (respectively) of human IL-4R. Amino acids −25 through −1 comprise a putative leader peptide; cleavage has been found to occur between amino acids −1 and 1, and between amino acids −3 and −2. Amino acids 208 through 231 form a transmembrane region. DNA encoding sIL-4R from amino acid −25 to amino acid 207 was used in the expression vectors.

The original expression vector, pCAVDHFR is a derivative of pCD302 (Mosley et al., *Cell* 89:335–348; 1989) containing the coding sequence for mouse DHFR (Subramani et al., *Mol. Cell. Biol.* 1:854, 1981). The pCDE vector is a derivative of pCAVDHFR containing the murine encephalomyocarditis virus IRES (nucleotides 260 through 824; Jang and Wimmer, *Genes and Dev.* 4:1560, 1990) cloned between the adenovirus tripartite leader and the DHFR cDNA coding sequence. An expression-augmenting sequence element (EASE) was included upstream of the CMV leader. The EASE is described in U.S. Pat. No. 6,027,915, issued Feb. 22, 2000, and in U.S. Ser. No. 09/435,377, filed Nov. 5, 1999, now allowed.

Figure 1:
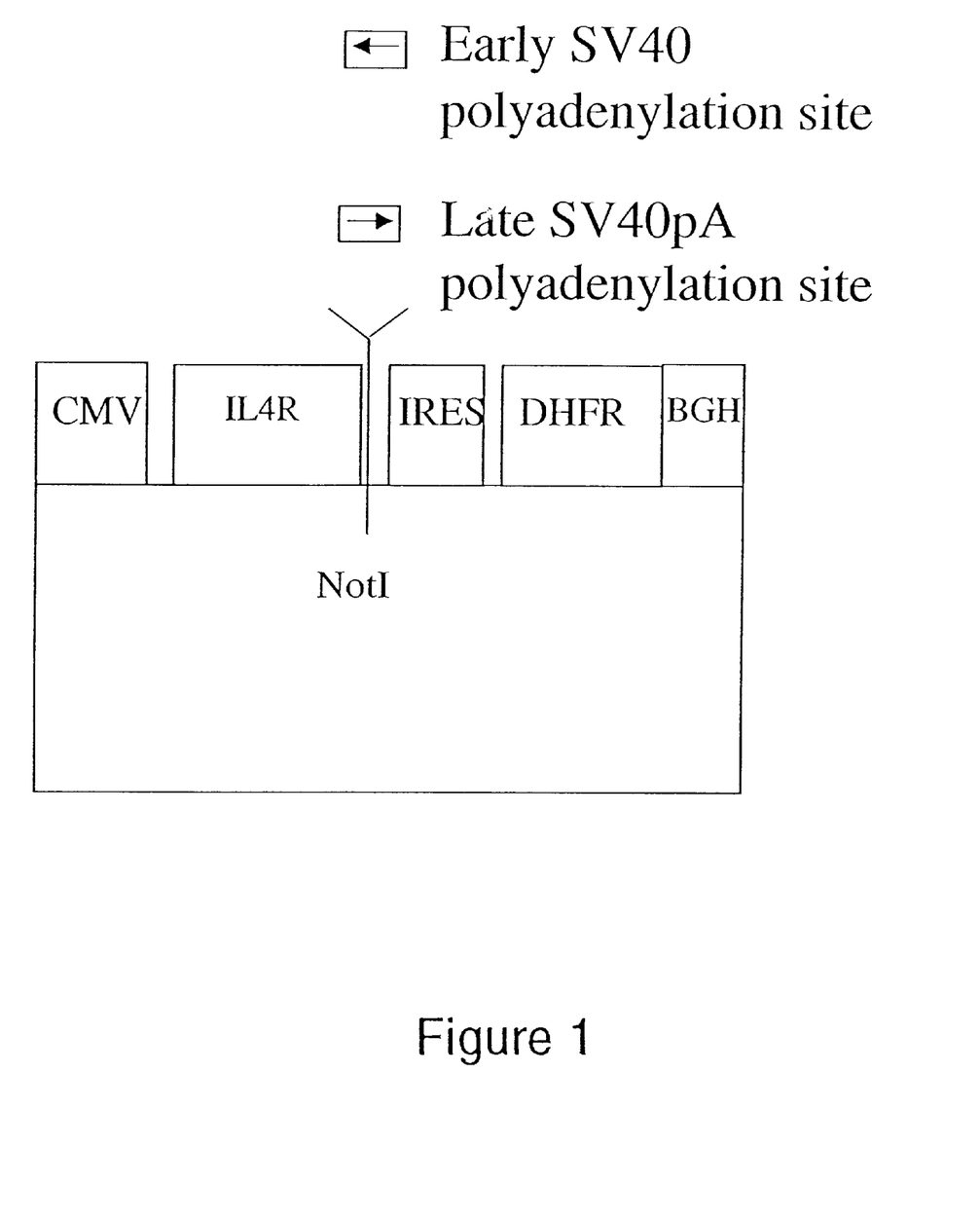
FIG. 1 is a diagram of constructs prepared in Example 1. The construct in which the SV40 early polyadenylation signal was included was designated SPA6; that in which the late polyadenylation signal was included was designated SPA4. A control construct was designated BGH.

To allow polyadenylation of the dicistronic message, the bovine growth hormone polyadenylation site was placed 3' of the DHFR gene. The plasmid pBGH is a standard dicistronic vector and serves as the control. The alternate polyadenylation vectors of the present invention were constructed by inserting various polyadenylation sites between the IL-4R and the IRES. The plasmids pSPA4, pSPA6, and pMLPA were constructed by inserting the late SV40 polyA site, the early SV40 polyA site, and a deletion mutant of the late SV40 polyA site, respectively. The deletion mutant late SV40 polyA site was constructed using PCR to isolate a fragment of the late SV40 polyA, nucleotides 80 through 222 of SEQ ID NO:1. A diagram of the various constructs is shown in FIG. 1; the nucleotide sequences of the various polyA sites are shown in the Sequence Listing (SV40 late: SEQ ID NO:1; BGH: SEQ ID NO:2; SV40 early: SEQ ID NO:3).

The plasmids were used in standard transfections to prepare transfected cells expressing IL-4R. Dihydrofolate reductase (DHFR) deficient Chinese hamster ovary (CHO) cells DXB11 (Chasin and Urlaub, supra) cells were adapted to a DMEM:F12 based serum free medium supplemented with 2 mM L-glutamine, 90 mM thymidine, 90 mM hypoxanthine, 120 mM glycine, 5% Hy-soy peptone, and 100 mg/L insulin like growth factor 1 (Rassmussen et al., *Cytotechnology* 28:31–42, 1998). For DHFR selection and methotrexate amplifications, the cells were cultured in the same medium lacking thymidine hypoxanthine, and glycine. For methotrexate selection, methotrexate (MTX; Lederle Laboratories, Pearl River, N.Y.) is added to the selection medium at appropriate concentrations. If neomycin selection is employed, 400 µg/ml of G418 (Gibco, Grand Island, N.Y.) is included in the medium. The cells are transfected using calcium phosphate transfection (Wigler et al. supra), or Lipofectamine™ transfection as recommended by the supplier (Gibco BRL, Gaithersburg, Md.). Lipofectamine™ Reagent is a commercially available reagent used to form lipid-nucleic acid complexes (or liposomes) which, when applied to cultured cells, facilitate uptake of the nucleic acid into the cells.

Example 2

This example describes a semi-quantitive polymerase chain reaction (PCR) technique that was used to confirm that the IL-4R and DHFR messages encoded by the plasmids described above were made and provide information on the relative levels of the various mRNAs. Cells were transfected and cultured as described, and mRNA was obtained using an RNeasy total RNA isolation kit (Quiagen, Chatsworth, Calif.), and treated with RNAse-free DNAse to diminish DNA contamination. Oligo-dT primers were used to prepare the first strand cDNA; a control primer for actin was included to facilitate quantification.

The first strand was amplified and the amount of input RNA determined using a GeneAmp 5700 from PE Biosystems (Foster City, Calif.). Thirty cycles of PCR were performed and real-time quantitation of the PCR products was achieved using the double-stranded DNA binding dye SYBR Green I (PE Biosystems, Foster City, Calif.). A standard curve was prepared using known amounts of actin cDNA, IL-4R cDNA, and DHFR cDNA. The amount of cDNA in each sample was normalized using the amount of actin cDNA. The relative amounts of IL-4R and DHFR in each sample are shown in Table 2.

TABLE 2

| Construct | IL-4R/Actin | DHFR/Actin |
| --- | --- | --- |
| pBGH | 4.2 | 7.4 |
| pMPLA | 32.5 | 2.0 |

These data demonstrate that cells transfected with the alternate polyadenylation vector have about 8 times as much IL-4R specific message as the control, and the amount of DHFR is reduced 3.5-fold relative to the control. This technique can be used to evaluate additional polyadenylation signals for use in the inventive expression vectors.

Example 3

This example describes an enzyme-linked immunosorbent assay (ELISA) that can be used to monitor production of recombinant proteins. The ELISA is well known in the art; adaptations of the techniques disclosed in Engvall et al., *Inmunochem.* 8:871, 1971 and in U.S. Pat. No. 4,703,004 have been used to monitor production of various recombinant proteins. In this assay, a first antibody specific for a protein of interest (usually a monoclonal antibody) is immobilized on a substrate (most often, a 96-well microtiter plate), then a sample containing the protein is added and incubated. A series of dilutions of a known concentration of the protein is also added and incubated, to yield a standard curve. After a wash step to remove unbound proteins and other materials, a second antibody to the protein is added. The second antibody is directed against a different epitope of the protein, and may be either a monoclonal antibody or a polyclonal antibody.

A conjugate reagent comprising an antibody that binds to the second antibody conjugated to an enzyme such as horse radish peroxidase (HRP) is added, either after a second wash step to remove unbound protein, or at the same time the second antibody is added. Following a suitable incubation period, unbound conjugate reagent is removed by washing, and a developing solution containing the substrate for the enzyme conjugate is added to the plate, causing color to develop. The optical density readings at the correct wavelength give numerical values for each well. The values for the sample are compared with the standard curve values, permitting levels of the desired protein to be quantitated.

To quantitate sIL-4R, an ELISA using two monoclonal antibodies (MAb) directed to different epitopes of IL-4R was developed. The first MAb (referred to as M10) was adsorbed onto plates overnight, and the peroxidase (HRP) conjugated second antibody (referred to as HRP-M8) was added after a wash step.

Example 4

This example describes the transfection of CHO cells with various constructs and compares the production of sIL-4R by pools of transfected cells. The various sIL-4R expression plasmids were transfected into CHO cells using Lipofectamine™. Cells were first selected for the DHFR+ phenotype, then pooled and selected at different MTX concentrations. Pools of cells were grown for two to three days, then supernatant fluid harvested and analyzed by ELISA as described in Example 3, and specific productivity (defined as $\mu$g of protein produced per day by $10^6$ cells) was determined. The results of a representative experiment are shown in Table 3 below.

TABLE 3

| Construct | Cells/ml × $10^6$ | % Viable | ELISA ($\mu$g protein) | Specific Productivity $\mu$g/$10^6$ cells/day |
| --- | --- | --- | --- | --- |
| BGH, Control | 1.98 | 94 | 0.3 | 0.12 |
| SPA4, SV40 late | 1.57 | 89 | 2.3 | 1.11 |
| SPA6, SV40 early | 2.42 | 91 | 3.2 | 1.10 |
| MLPA | 1.81 | 92 | 2.5 | 1.08 |
| PY, Polyoma virus | 2.4 | 93 | 0.4 | 0.14 |

These results demonstrated that the insertion of internal polyA sites in between a DNA encoding a desired recombinant protein and a DNA encoding a selectable marker can enhance expression of the desired recombinant protein from pools of transfected cells.

Example 5

This example illustrates the production of sIL-4R by pools of transfected CHO cells over time. A high level of expression was stable over many passages. Four independent transfections with the MLPA plasmid were performed substantially as described previously, and passaged over 20 generations. Expression was monitored from each culture individually, and specific productivity results were averaged; the averages are shown in Table 4.

TABLE 4

| Passage number | Specific Productivity $\mu$g/$10^6$ cells/day | Standard deviation |
| --- | --- | --- |
| 5 | 1.22 | 0.41 |
| 10 | 1.26 | 0.39 |
| 15 | 1.18 | 0.55 |
| 18 | 1.09 | 0.49 |
| 20 | 1.02 | 0.62 |

As can be seen in the data from Table 4, expression remained stable over 20 passages. Cells from passage 20 from two of the pools were then amplified in 5 nm methotrexate and monitored for IL-4R expression; results are shown in Table 5. Amplified pools exhibited increased expression when compared to the unamplified pools.

TABLE 5

| Passage number | Specific Productivity Pool #1 | Specific Productivity Pool #2 |
| --- | --- | --- |
| 27 | 1.95 | 1.37 |
| 29 | 2.10 | 1.58 |
| 33 | 2.08 | 1.42 |

Example 6

This example illustrates the effect of internal polyA sites on clones of cells derived from transfected pools. BGH, SPA4 and SPA6 cells were cloned by limiting dilution in the presence of MTX. Several colonies were picked and screened for specific productivity of sIL-4R as described for the pools. Results are shown in Table 6.

TABLE 6

| Construct | Clone # | MTX Concentration | Cells/ml | % Viable | ELISA (μg protein) | Specific Productivity μg/10⁶ cells/day |
|---|---|---|---|---|---|---|
| BGH | 3 | 200 | 1.84 | 69 | 14.6 | 4.25 |
| SPA4 | 2 | 50 | 2.26 | 89 | 16.2 | 3.99 |
| SPA6 | 10 | 100 | 1.82 | 94 | 1.6 | 0.47 |
| SPA6 | 11 | 100 | 1.46 | 83 | 7 | 2.44 |
| SPA6 | 13 | 100 | 0.96 | 67 | 9.3 | 4.40 |
| SPA6 | 16 | 100 | 1.02 | 73 | 0 | 0 |

These results demonstrate that the clones picked from the pools transfected with expression vectors comprising an internal polyA site can express high levels of the desired recombinant protein. For the purposes of producing large amounts of recombinant protein for use as a pharmaceutical, clones are often reamplified in methotrexate. In order to evaluate the effect of an internal polyA site on the reamplification process, clone 2 from the SPA4 pool was reamplified by culturing the cells for several passages in increasing concentrations of methotrexate. Once the cells had recovered from the methotrexate amplification with viabilities of about 90%, the specific productivity was determined by culturing the cells for two to three days, harvesting the supernatant fluid, and assaying the supernatant fluid for IL-4R by ELISA; results are shown in Table 7.

TABLE 7

| Construct | Methotrexate Concentration | Cells/ml | % Viable | ELISA (μg protein) | Specific Productivity μg/10⁶ cells/day |
|---|---|---|---|---|---|
| SPA4-2 | 50 nM | 2.32 | 94 | 18.7 | 4.58 |
| SPA4-2 | 100 nM | 1.66 | 91 | 21.1 | 6.83 |
| SPA4-2 | 150 nM | 1.95 | 90 | 27.7 | 7.86 |
| SPA4-2 | 200 nM | 1.93 | 91 | 28.8 | 8.24 |

These results demonstrated that clones of cells transfected with expression vectors comprising an internal polyA site can be reamplified, and will be expected to evince higher specific productivity.

Example 7

This example describes the preparation of several expression vectors for the expression of recombinant proteins. An expression vector encoding a marker protein (secreted alkaline phosphatase or SEAP; Berger et al., Gene 66:1, 1988) is prepared substantially as described previously, using the MLPA polyA site internally; a polyA site other than BGH may be used as the terminal polyA site. Several changes are made to the IRES sequence within the expression vectors. As discussed in Davies and Kaufman (J. Virology 66:1924; 1992), the efficiency of translation of a second gene can be manipulated by altering the sequence of the IRES at or near the junction of the IRES with the second gene, in this case, DHFR. Table 8 depicts the nucleotide sequence added to the IRES; the first base indicated in the Table is directly after nucleotide 566 of the EMCV IRES (SEQ ID NO:7). Translational start sites (ATG) are underlined; the 3'ATG is the first ATG of muDHFR.

TABLE 8

| Construct | DNA Sequence at IRES DHFR junction | |
|---|---|---|
| IX-312 | ATTGCTCGAGATCCGTGCCATC<u>ATG</u> | (SEQ ID NO:8) |
| IXED-1 | <u>ATG</u>ATAAT<u>ATG</u> | (SEQ ID NO:9) |
| IXED-3 | <u>ATG</u>ATAAT<u>ATG</u>GCCACAACC<u>ATG</u> | (SEQ ID NO:10) |

Appending the nucleotide sequences to the IRES will modulate expression of DHFR sufficiently to increase the percentage of cells transfected without significantly decreasing the levels of the desired recombinant protein. The vectors (including control vectors) are used in standard transfections to prepare transfected cells expressing SEAP substantially as described herein. Expression levels of the marker protein, SEAP, are determined using a quantitative assay such as that available from CLONTECH Laboratories (Palo Alto, Calif., USA; Yang et al., Biotechniques 2:1110, 1997).

What is claimed is:

1. An expression vector comprising, in the following order, a promoter sequence, a first coding sequence, a polyadenylation site, and a second coding sequence operably linked to the first coding sequence, wherein no promoter sequence occurs between the polyadenylation site and the second coding sequence.

2. The expression vector of claim 1, wherein the second coding sequence encodes a selectable marker.

3. The expression vector of claim 2, wherein the selectable marker is dihydrofolate reductase.

4. The expression vector of claim 1 wherein the polyadenylation site comprises a sequence selected from the group consisting of SEQ ID NO:1, SEQ ID NO:3, and residues 80 through 222 of SEQ ID NO:1.

5. The expression vector of claim 2 wherein the polyadenylation site comprises a sequence selected from the group consisting of SEQ ID NO:1, SEQ ID NO:3, and residues 80 through 222 of SEQ ID NO:1.

6. The expression vector of claim 3 wherein the polyadenylation site comprises a sequence selected from the group consisting of SEQ ID NO:1, SEQ ID NO:3, and residues 80 through 222 of SEQ ID NO:1.

7. The expression vector of claim 1 wherein an internal ribosome entry site (IRES) is inserted between the polyadenylation site and the second coding sequence such that the IRES is operably linked to the second coding sequence.

8. The expression vector of claim 2 wherein an internal ribosome entry site (IRES) is inserted between the polyadenylation site and the selectable marker such that the IRES is operably linked to the selectable marker.

9. The expression vector of claim 3 wherein an internal ribosome entry site (IRES) is inserted between the polyadenylation site and the selectable marker such that the IRES is operably linked to the selectable marker.

10. The expression vector of claim 4 wherein an internal ribosome entry site (IRES) is inserted between the polyadenylation site and the second coding sequence such that the IRES is operably linked to the second coding sequence.

11. The expression vector of claim 5 wherein an internal ribosome entry site (IRES) is inserted between the polyadenylation site and the selectable marker such that the IRES is operably linked to the selectable marker.

12. The expression vector of claim 6 wherein an internal ribosome entry site (IRES) is inserted between the polyadenylation site and the selectable marker such that the IRES is operably linked to the selectable marker.

13. A stable pools of cells transfected with the expression vector according to claim 7.

14. A stable pools of cells transfected with the expression vector according to claim 8.

15. A stable pools of cells transfected with the expression vector according to claim 9.

16. A stable pools of cells transfected with the expression vector according to claim 10.

17. A stable pools of cells transfected with the expression vector according to claim 11.

18. A stable pools of cells transfected with the expression vector according to claim 12.

19. A method for obtaining a recombinant protein, comprising culturing a cell line according to claim 18 under conditions promoting expression of the protein, and recovering the protein.

20. A method for obtaining a recombinant protein, comprising culturing a cell line according to claim 18 under conditions promoting expression of the protein, and recovering the protein.

21. A method for obtaining a recombinant protein, comprising culturing a cell line according to claim 18 conditions promoting expression of the protein, and recovering the protein.

22. A method for obtaining a recombinant protein, comprising culturing a cell line according to claim 18 under conditions promoting expression of the protein, and recovering the protein.

23. A method for obtaining a recombinant protein, comprising culturing a cell line according to claim 18 under conditions promoting expression of the protein, and recovering the protein.

24. A method for obtaining a recombinant protein, comprising culturing a cell line according to claim 18 under conditions promoting expression of the protein, and recovering the protein.

25. The expression vector of claim 1, which further comprises a second polyadenylation site following the second coding sequence and operably linked thereto.

26. An expression vector comprising, in the following order, a promoter sequence, a first coding sequence, a polyadenylation site comprising nucleotides 123 through 128 and 151 through 187 of SEQ ID NO:1, and a second coding sequence, wherein no promoter sequence occurs between the polyadenylation site and the second coding sequence.

27. A stable pool of mammalian cells transfected with an expression vector according to claim 26.

28. A cell line cloned from the pool of claim 27.

29. A mammalian host cell containing an expression vector according to claim 7.

30. A mammalian host cell containing an expression vector according to claim 8.

31. A mammalian host cell containing an expression vector according to claim 9.

32. A mammalian host cell containing an expression vector according to claim 10.

33. A mammalian host cell containing an expression vector according to claim 11.

34. A mammalian host cell containing an expression vector according to claim 26.

35. The expression vector of claim 26, which further comprises a second polyadenylation site following the second coding sequence and operably linked thereto.

36. A mammalian host cell containing the expression vector of claim 35.

37. A stable pools of cells transfected with the expression vector of claim 35.

38. A cell line cloned from the pool of claim 37.

39. The mammalian host cell of claim 29, wherein the first coding sequence encodes a recombinant protein.

40. The mammalian host cell of claim 30, wherein the first coding sequence encodes a recombinant protein.

41. The mammalian host cell of claim 31, wherein the first coding sequence encodes a recombinant protein.

42. The mammalian host cell of claim 32, wherein the first coding sequence encodes a recombinant protein.

43. The mammalian host cell of claim 33, wherein the first coding sequence encodes a recombinant protein.

44. The mammalian host cell of claim 34, wherein the first coding sequence encodes a recombinant protein.

* * * * *

SEQUENCE LISTING

<160> NUMBER OF SEQ ID NOS: 10

<210> SEQ ID NO 1
<211> LENGTH: 222
<212> TYPE: DNA
<213> ORGANISM: SV40

<400> SEQUENCE: 1

```
atccagacat gataagatac attgatgagt ttggacaaac cacaactaga atgcagtgaa      60
aaaaatgctt tatttgtgaa atttgtgatg ctattgcttt atttgtaacc attataagct     120
gcaataaaca agttcaacaa caattgcatt cattttatgt ttcaggttca gggggaggtg     180
```

-continued

```
tgggaggttt tttaaagcaa gtaaaacctc tacaaatgtg gt                          222
```

<210> SEQ ID NO 2
<211> LENGTH: 285
<212> TYPE: DNA
<213> ORGANISM: Bovine

<400> SEQUENCE: 2

```
aattgtctag agctcgctga tcagcctcga ctgtgccttc tagttgccag ccatctgttg        60
tttgccccct cccccgtgcct tccttgaccc tggaaggtgc cactcccact gtcctttcct     120
aataaaatga ggaaattgca tcgcattgtc tgagtaggtg tcattctatt ctgggggggtg     180
gggtggggca ggacagcaag ggggaggatt gggaagacaa tagcaggcat gctggggatg      240
cggtgggctc tatggcttct gaggcggaaa gaaccagctg ggca                       285
```

<210> SEQ ID NO 3
<211> LENGTH: 222
<212> TYPE: DNA
<213> ORGANISM: SV40

<400> SEQUENCE: 3

```
accacatttg tagaggtttt acttgcttta aaaaacctcc cacacctccc cctgaacctg        60
aaacataaaa tgaatgcaat tgttgttgaa cttgtttatt gcagcttata atggttacaa      120
ataaagcaat agcatcacaa atttcacaaa taaagcattt ttttcactgc attctagttg      180
tggtttgtcc aaactcatca atgtatctta tcatgtctgg at                         222
```

<210> SEQ ID NO 4
<211> LENGTH: 19
<212> TYPE: RNA
<213> ORGANISM: RNA recognition sequence

<400> SEQUENCE: 4

```
acaugaggau uacccaugu                                                    19
```

<210> SEQ ID NO 5
<211> LENGTH: 2478
<212> TYPE: DNA
<213> ORGANISM: Homo sapiens
<220> FEATURE:
<221> NAME/KEY: CDS
<222> LOCATION: (1)..(2478)
<221> NAME/KEY: mat_peptide
<222> LOCATION: (76)..()
<221> NAME/KEY: sig_peptide
<222> LOCATION: (1)..(75)

<400> SEQUENCE: 5

```
atg ggg tgg ctt tgc tct ggg ctc ctg ttc cct gtg agc tgc ctg gtc         48
Met Gly Trp Leu Cys Ser Gly Leu Leu Phe Pro Val Ser Cys Leu Val
-25                 -20                 -15                 -10 ctg ctg cag gtg gca agc tct ggg aac atg aag gtc ttg cag gag ccc         96
Leu Leu Gln Val Ala Ser Ser Gly Asn Met Lys Val Leu Gln Glu Pro
            -5                  -1  1                   5 acc tgc gtc tcc gac tac atg agc atc tct act tgc gag tgg aag atg       144
Thr Cys Val Ser Asp Tyr Met Ser Ile Ser Thr Cys Glu Trp Lys Met
            10                  15                  20 aat ggt ccc acc aat tgc agc acc gag ctc cgc ctg ttg tac cag ctg       192
Asn Gly Pro Thr Asn Cys Ser Thr Glu Leu Arg Leu Leu Tyr Gln Leu
        25                  30                  35 gtt ttt ctg ctc tcc gaa gcc cac acg tgt atc cct gag aac aac gga       240
Val Phe Leu Leu Ser Glu Ala His Thr Cys Ile Pro Glu Asn Asn Gly
```

```
                                                                -continued 40                      45                      50                      55 ggc gcg ggg tgc gtg tgc cac ctg ctc atg gat gac gtg gtc agt gcg          288
Gly Ala Gly Cys Val Cys His Leu Leu Met Asp Asp Val Val Ser Ala
                60                      65                      70 gat aac tat aca ctg gac ctg tgg gct ggg cag cag ctg ctg tgg aag          336
Asp Asn Tyr Thr Leu Asp Leu Trp Ala Gly Gln Gln Leu Leu Trp Lys
            75                      80                      85 ggc tcc ttc aag ccc agc gag cat gtg aaa ccc agg gcc cca gga aac          384
Gly Ser Phe Lys Pro Ser Glu His Val Lys Pro Arg Ala Pro Gly Asn
        90                      95                     100 ctg aca gtt cac acc aat gtc tcc gac act ctg ctg acc tgg agc              432
Leu Thr Val His Thr Asn Val Ser Asp Thr Leu Leu Leu Thr Trp Ser
    105                     110                     115 aac ccg tat ccc cct gac aat tac ctg tat aat cat ctc acc tat gca          480
Asn Pro Tyr Pro Pro Asp Asn Tyr Leu Tyr Asn His Leu Thr Tyr Ala
120                     125                     130                     135 gtc aac att tgg agt gaa aac gac ccg gca gat ttc aga atc tat aac          528
Val Asn Ile Trp Ser Glu Asn Asp Pro Ala Asp Phe Arg Ile Tyr Asn
                140                     145                     150 gtg acc tac cta gaa ccc tcc ctc cgc atc gca gcc agc acc ctg aag          576
Val Thr Tyr Leu Glu Pro Ser Leu Arg Ile Ala Ala Ser Thr Leu Lys
            155                     160                     165 tct ggg att tcc tac agg gca cgg gtg agg gcc tgg gct cag tgc tat          624
Ser Gly Ile Ser Tyr Arg Ala Arg Val Arg Ala Trp Ala Gln Cys Tyr
        170                     175                     180 aac acc acc tgg agt gag tgg agc ccc agc acc aag tgg cac aac tcc          672
Asn Thr Thr Trp Ser Glu Trp Ser Pro Ser Thr Lys Trp His Asn Ser
    185                     190                     195 tac agg gag ccc ttc gag cag cac ctc ctg ctg ggc gtc agc gtt tcc          720
Tyr Arg Glu Pro Phe Glu Gln His Leu Leu Leu Gly Val Ser Val Ser
200                     205                     210                     215 tgc att gtc atc ctg gcc gtc tgc ctg ttg tgc tat gtc agc atc acc          768
Cys Ile Val Ile Leu Ala Val Cys Leu Leu Cys Tyr Val Ser Ile Thr
                220                     225                     230 aag att aag aaa gaa tgg tgg gat cag att ccc aac cca gcc cgc agc          816
Lys Ile Lys Lys Glu Trp Trp Asp Gln Ile Pro Asn Pro Ala Arg Ser
            235                     240                     245 cgc ctc gtg gct ata ata atc cag gat gct cag ggg tca cag tgg gag          864
Arg Leu Val Ala Ile Ile Ile Gln Asp Ala Gln Gly Ser Gln Trp Glu
        250                     255                     260 aag cgg tcc cga ggc cag gaa cca gcc aag tgc cca cac tgg aag aat          912
Lys Arg Ser Arg Gly Gln Glu Pro Ala Lys Cys Pro His Trp Lys Asn
    265                     270                     275 tgt ctt acc aag ctc ttg ccc tgt ttt ctg gag cac aac atg aaa agg          960
Cys Leu Thr Lys Leu Leu Pro Cys Phe Leu Glu His Asn Met Lys Arg
280                     285                     290                     295 gat gaa gat cct cac aag gct gcc aaa gag atg cct ttc cag ggc tct         1008
Asp Glu Asp Pro His Lys Ala Ala Lys Glu Met Pro Phe Gln Gly Ser
                300                     305                     310 gga aaa tca gca tgg tgc cca gtg gag atc agc aag aca gtc ctc tgg         1056
Gly Lys Ser Ala Trp Cys Pro Val Glu Ile Ser Lys Thr Val Leu Trp
            315                     320                     325 cca gag agc atc agc gtg gtg cga tgt gtg gag ttg ttt gag gcc ccg         1104
Pro Glu Ser Ile Ser Val Val Arg Cys Val Glu Leu Phe Glu Ala Pro
        330                     335                     340 gtg gag tgt gag gag gag gag gta gag gaa gaa aaa ggg agc ttc             1152
Val Glu Cys Glu Glu Glu Glu Val Glu Glu Glu Lys Gly Ser Phe
    345                     350                     355 tgt gca tcg cct gag agc agc agg gat gac ttc cag gag gga agg gag         1200
```

```
Cys Ala Ser Pro Glu Ser Ser Arg Asp Asp Phe Gln Glu Gly Arg Glu
360             365                 370                 375 ggc att gtg gcc cgg cta aca gag agc ctg ttc ctg gac ctg ctc gga      1248
Gly Ile Val Ala Arg Leu Thr Glu Ser Leu Phe Leu Asp Leu Leu Gly
                380                 385                 390 gag gag aat ggg ggc ttt tgc cag cag gac atg ggg gag tca tgc ctt      1296
Glu Glu Asn Gly Gly Phe Cys Gln Gln Asp Met Gly Glu Ser Cys Leu
            395                 400                 405 ctt cca cct tcg gga agt acg agt gct cac atg ccc tgg gat gag ttc      1344
Leu Pro Pro Ser Gly Ser Thr Ser Ala His Met Pro Trp Asp Glu Phe
        410                 415                 420 cca agt gca ggg ccc aag gag gca cct ccc tgg ggc aag gag cag cct      1392
Pro Ser Ala Gly Pro Lys Glu Ala Pro Pro Trp Gly Lys Glu Gln Pro
    425                 430                 435 ctc cac ctg gag cca agt cct cct gcc agc ccg acc cag agt cca gac      1440
Leu His Leu Glu Pro Ser Pro Pro Ala Ser Pro Thr Gln Ser Pro Asp
440                 445                 450                 455 aac ctg act tgc aca gag acg ccc ctc gtc atc gca ggc aac cct gct      1488
Asn Leu Thr Cys Thr Glu Thr Pro Leu Val Ile Ala Gly Asn Pro Ala
                460                 465                 470 tac cgc agc ttc agc aac tcc ctg agc cag tca ccg tgt ccc aga gag      1536
Tyr Arg Ser Phe Ser Asn Ser Leu Ser Gln Ser Pro Cys Pro Arg Glu
            475                 480                 485 ctg ggt cca gac cca ctg ctg gcc aga cac ctg gag gaa gta gaa ccc      1584
Leu Gly Pro Asp Pro Leu Leu Ala Arg His Leu Glu Glu Val Glu Pro
        490                 495                 500 gag atg ccc tgt gtc ccc cag ctc tct gag cca acc act gtg ccc caa      1632
Glu Met Pro Cys Val Pro Gln Leu Ser Glu Pro Thr Thr Val Pro Gln
    505                 510                 515 cct gag cca gaa acc tgg gag cag atc ctc cgc cga aat gtc ctc cag      1680
Pro Glu Pro Glu Thr Trp Glu Gln Ile Leu Arg Arg Asn Val Leu Gln
520                 525                 530                 535 cat ggg gca gct gca gcc ccc gtc tcg gcc ccc acc agt ggc tat cag      1728
His Gly Ala Ala Ala Ala Pro Val Ser Ala Pro Thr Ser Gly Tyr Gln
                540                 545                 550 gag ttt gta cat gcg gtg gag cag ggt ggc acc cag gcc agt gcg gtg      1776
Glu Phe Val His Ala Val Glu Gln Gly Gly Thr Gln Ala Ser Ala Val
            555                 560                 565 gtg ggc ttg ggt ccc cca gga gag gct ggt tac aag gcc ttc tca agc      1824
Val Gly Leu Gly Pro Pro Gly Glu Ala Gly Tyr Lys Ala Phe Ser Ser
        570                 575                 580 ctg ctt gcc agc agt gct gtg tcc cca gag aaa tgt ggg ttt ggg gct      1872
Leu Leu Ala Ser Ser Ala Val Ser Pro Glu Lys Cys Gly Phe Gly Ala
    585                 590                 595 agc agt ggg gaa gag ggg tat aag cct ttc caa gac ctc att cct ggc      1920
Ser Ser Gly Glu Glu Gly Tyr Lys Pro Phe Gln Asp Leu Ile Pro Gly
600                 605                 610                 615 tgc cct ggg gac cct gcc cca gtc cct gtc ccc ttg ttc acc ttt gga      1968
Cys Pro Gly Asp Pro Ala Pro Val Pro Val Pro Leu Phe Thr Phe Gly
                620                 625                 630 ctg gac agg gag cca cct cgc agt ccg cag agc tca cat ctc cca agc      2016
Leu Asp Arg Glu Pro Pro Arg Ser Pro Gln Ser Ser His Leu Pro Ser
            635                 640                 645 agc tcc cca gag cac ctg ggt ctg gag ccg ggg gaa aag gta gag gac      2064
Ser Ser Pro Glu His Leu Gly Leu Glu Pro Gly Glu Lys Val Glu Asp
        650                 655                 660 atg cca aag ccc cca ctt ccc cag gag cag gcc aca gac ccc ctt gtg      2112
Met Pro Lys Pro Pro Leu Pro Gln Glu Gln Ala Thr Asp Pro Leu Val
    665                 670                 675
```

```
gac agc ctg ggc agt ggc att gtc tac tca gcc ctt acc tgc cac ctg     2160
Asp Ser Leu Gly Ser Gly Ile Val Tyr Ser Ala Leu Thr Cys His Leu
680             685                 690                 695 tgc ggc cac ctg aaa cag tgt cat ggc cag gag gat ggt ggc cag acc     2208
Cys Gly His Leu Lys Gln Cys His Gly Gln Glu Asp Gly Gly Gln Thr
                700                 705                 710 cct gtc atg gcc agt cct tgc tgt ggc tgc tgc tgt gga gac agg tcc     2256
Pro Val Met Ala Ser Pro Cys Cys Gly Cys Cys Cys Gly Asp Arg Ser
            715                 720                 725 tcg ccc cct aca acc ccc ctg agg gcc cca gac ccc tct cca ggt ggg     2304
Ser Pro Pro Thr Thr Pro Leu Arg Ala Pro Asp Pro Ser Pro Gly Gly
        730                 735                 740 gtt cca ctg gag gcc agt ctg tgt ccg gcc tcc ctg gca ccc tcg ggc     2352
Val Pro Leu Glu Ala Ser Leu Cys Pro Ala Ser Leu Ala Pro Ser Gly
    745                 750                 755 atc tca gag aag agt aaa tcc tca tca tcc ttc cat cct gcc cct ggc     2400
Ile Ser Glu Lys Ser Lys Ser Ser Ser Ser Phe His Pro Ala Pro Gly
760                 765                 770                 775 aat gct cag agc tca agc cag acc ccc aaa atc gtg aac ttt gtc tcc     2448
Asn Ala Gln Ser Ser Ser Gln Thr Pro Lys Ile Val Asn Phe Val Ser
                780                 785                 790 gtg gga ccc aca tac atg agg gtc tct tat                             2478
Val Gly Pro Thr Tyr Met Arg Val Ser Tyr
            795                 800

<210> SEQ ID NO 6
<211> LENGTH: 826
<212> TYPE: PRT
<213> ORGANISM: Homo sapiens

<400> SEQUENCE: 6

Met Gly Trp Leu Cys Ser Gly Leu Leu Phe Pro Val Ser Cys Leu Val
-25             -20                 -15                 -10

Leu Leu Gln Val Ala Ser Ser Gly Asn Met Lys Val Leu Gln Glu Pro
                -5                  -1  1               5

Thr Cys Val Ser Asp Tyr Met Ser Ile Ser Thr Cys Glu Trp Lys Met
            10                  15                  20

Asn Gly Pro Thr Asn Cys Ser Thr Glu Leu Arg Leu Leu Tyr Gln Leu
        25                  30                  35

Val Phe Leu Leu Ser Glu Ala His Thr Cys Ile Pro Glu Asn Asn Gly
40                  45                  50                  55

Gly Ala Gly Cys Val Cys His Leu Leu Met Asp Asp Val Val Ser Ala
                60                  65                  70

Asp Asn Tyr Thr Leu Asp Leu Trp Ala Gly Gln Gln Leu Leu Trp Lys
            75                  80                  85

Gly Ser Phe Lys Pro Ser Glu His Val Lys Pro Arg Ala Pro Gly Asn
        90                  95                  100

Leu Thr Val His Thr Asn Val Ser Asp Thr Leu Leu Leu Thr Trp Ser
    105                 110                 115

Asn Pro Tyr Pro Pro Asp Asn Tyr Leu Tyr Asn His Leu Thr Tyr Ala
120                 125                 130                 135

Val Asn Ile Trp Ser Glu Asn Asp Pro Ala Asp Phe Arg Ile Tyr Asn
                140                 145                 150

Val Thr Tyr Leu Glu Pro Ser Leu Arg Ile Ala Ala Ser Thr Leu Lys
            155                 160                 165

Ser Gly Ile Ser Tyr Arg Ala Arg Val Arg Ala Trp Ala Gln Cys Tyr
        170                 175                 180
```

-continued

```
Asn Thr Thr Trp Ser Glu Trp Ser Pro Ser Thr Lys Trp His Asn Ser
185                 190                 195
Tyr Arg Glu Pro Phe Glu Gln His Leu Leu Leu Gly Val Ser Val Ser
200                 205                 210                 215
Cys Ile Val Ile Leu Ala Val Cys Leu Leu Cys Tyr Val Ser Ile Thr
                220                 225                 230
Lys Ile Lys Lys Glu Trp Trp Asp Gln Ile Pro Asn Pro Ala Arg Ser
            235                 240                 245
Arg Leu Val Ala Ile Ile Gln Asp Ala Gln Gly Ser Gln Trp Glu
        250                 255                 260
Lys Arg Ser Arg Gly Gln Glu Pro Ala Lys Cys Pro His Trp Lys Asn
    265                 270                 275
Cys Leu Thr Lys Leu Leu Pro Cys Phe Leu Glu His Asn Met Lys Arg
280                 285                 290                 295
Asp Glu Asp Pro His Lys Ala Ala Lys Glu Met Pro Phe Gln Gly Ser
                300                 305                 310
Gly Lys Ser Ala Trp Cys Pro Val Glu Ile Ser Lys Thr Val Leu Trp
            315                 320                 325
Pro Glu Ser Ile Ser Val Val Arg Cys Val Glu Leu Phe Glu Ala Pro
        330                 335                 340
Val Glu Cys Glu Glu Glu Glu Val Glu Glu Lys Gly Ser Phe
345                 350                 355
Cys Ala Ser Pro Glu Ser Ser Arg Asp Asp Phe Gln Glu Gly Arg Glu
360                 365                 370                 375
Gly Ile Val Ala Arg Leu Thr Glu Ser Leu Phe Leu Asp Leu Leu Gly
                380                 385                 390
Glu Glu Asn Gly Gly Phe Cys Gln Gln Asp Met Gly Glu Ser Cys Leu
            395                 400                 405
Leu Pro Pro Ser Gly Ser Thr Ser Ala His Met Pro Trp Asp Glu Phe
        410                 415                 420
Pro Ser Ala Gly Pro Lys Glu Ala Pro Pro Trp Gly Lys Glu Gln Pro
    425                 430                 435
Leu His Leu Glu Pro Ser Pro Pro Ala Ser Pro Thr Gln Ser Pro Asp
440                 445                 450                 455
Asn Leu Thr Cys Thr Glu Thr Pro Leu Val Ile Ala Gly Asn Pro Ala
                460                 465                 470
Tyr Arg Ser Phe Ser Asn Ser Leu Ser Gln Ser Pro Cys Pro Arg Glu
            475                 480                 485
Leu Gly Pro Asp Pro Leu Leu Ala Arg His Leu Glu Glu Val Glu Pro
        490                 495                 500
Glu Met Pro Cys Val Pro Gln Leu Ser Glu Pro Thr Thr Val Pro Gln
    505                 510                 515
Pro Glu Pro Glu Thr Trp Glu Gln Ile Leu Arg Arg Asn Val Leu Gln
520                 525                 530                 535
His Gly Ala Ala Ala Pro Val Ser Ala Pro Thr Ser Gly Tyr Gln
                540                 545                 550
Glu Phe Val His Ala Val Glu Gln Gly Gly Thr Gln Ala Ser Ala Val
            555                 560                 565
Val Gly Leu Gly Pro Pro Gly Glu Ala Gly Tyr Lys Ala Phe Ser Ser
        570                 575                 580
Leu Leu Ala Ser Ser Ala Val Ser Pro Glu Lys Cys Gly Phe Gly Ala
    585                 590                 595
Ser Ser Gly Glu Glu Gly Tyr Lys Pro Phe Gln Asp Leu Ile Pro Gly
```

```
            600              605              610              615

Cys Pro Gly Asp Pro Ala Pro Val Pro Val Pro Leu Phe Thr Phe Gly
                       620              625              630

Leu Asp Arg Glu Pro Pro Arg Ser Pro Gln Ser Ser His Leu Pro Ser
                       635              640              645

Ser Ser Pro Glu His Leu Gly Leu Glu Pro Gly Glu Lys Val Glu Asp
                   650              655              660

Met Pro Lys Pro Pro Leu Pro Gln Glu Gln Ala Thr Asp Pro Leu Val
               665              670              675

Asp Ser Leu Gly Ser Gly Ile Val Tyr Ser Ala Leu Thr Cys His Leu
       680              685              690              695

Cys Gly His Leu Lys Gln Cys His Gly Gln Glu Asp Gly Gly Gln Thr
                       700              705              710

Pro Val Met Ala Ser Pro Cys Cys Gly Cys Cys Cys Gly Asp Arg Ser
                       715              720              725

Ser Pro Pro Thr Thr Pro Leu Arg Ala Pro Asp Pro Ser Pro Gly Gly
                   730              735              740

Val Pro Leu Glu Ala Ser Leu Cys Pro Ala Ser Leu Ala Pro Ser Gly
               745              750              755

Ile Ser Glu Lys Ser Lys Ser Ser Ser Phe His Pro Ala Pro Gly
       760              765              770              775

Asn Ala Gln Ser Ser Ser Gln Thr Pro Lys Ile Val Asn Phe Val Ser
                       780              785              790

Val Gly Pro Thr Tyr Met Arg Val Ser Tyr
                   795              800

<210> SEQ ID NO 7
<211> LENGTH: 566
<212> TYPE: DNA
<213> ORGANISM: EMCV

<400> SEQUENCE: 7
cccctctccc tcccccccc ctaacgttac tggccgaagc cgcttggaat aaggccggtg      60
tgcgtttgtc tatatgttat tttccaccat attgccgtct tttggcaatg tgagggcccg    120
gaaacctggc cctgtcttct tgacgagcat tcctaggggt cttccctc tcgccaaagg      180 aatgcaagt ctgttgaatg tcgtgaagga agcagttcct ctggaagctt cttgaagaca     240
aacaacgtct gtagcgaccc tttgcaggca gcggaacccc ccacctggcg acaggtgcct    300
ctgcggccaa agccacgtg tataagatac acctgcaaag gcggcacaac cccagtgcca     360
cgttgtgagt tggatagttg tggaaagagt caaatggctc tcctcaagcg tattcaacaa    420
ggggctgaag gatgcccaga aggtacccca ttgtatggga tctgatctgg ggcctcggtg    480
cacatgcttt acatgtgttt agtcgaggtt aaaaaacgtc taggcccccc gaaccacggg    540
gacgtggttt tcctttgaaa aacacg                                         566

<210> SEQ ID NO 8
<211> LENGTH: 25
<212> TYPE: DNA
<213> ORGANISM: EMCV

<400> SEQUENCE: 8
attgctcgag atccgtgcca tcatg                                           25

<210> SEQ ID NO 9
<211> LENGTH: 11
```

```
<212> TYPE: DNA
<213> ORGANISM: EMCV

<400> SEQUENCE: 9
atgataatat g                                                        11

<210> SEQ ID NO 10
<211> LENGTH: 23
<212> TYPE: DNA
<213> ORGANISM: EMCV

<400> SEQUENCE: 10
atgataatat ggccacaacc atg                                           23
```